(12) United States Patent
Leonardi et al.

(10) Patent No.: US 12,329,725 B2
(45) Date of Patent: Jun. 17, 2025

(54) USE OF A LIGNIN FRACTION AS A HUMAN AND ANIMAL FOOD SUPPLEMENT INGREDIENT

(71) Applicants: GREEN INNOVATION GMBH, Innsbruck (AT); UPM-KYMMENE CORPORATION, Helsinki (FI)

(72) Inventors: Giuliano Leonardi, Innsbruck (AT); Suvi Pietarinen, Helsinki (FI); Christian Hübsch, Helsinki (FI)

(73) Assignees: GREEN INNOVATION GMBH, Innsbruck (AT); UPM-KYMMENE CORPORATION, Helsinki (FI)

( * ) Notice: Subject to any disclaimer, the term of this patent is extended or adjusted under 35 U.S.C. 154(b) by 278 days.

(21) Appl. No.: 16/955,960

(22) PCT Filed: Dec. 11, 2018

(86) PCT No.: PCT/EP2018/084310
§ 371 (c)(1),
(2) Date: Jun. 19, 2020

(87) PCT Pub. No.: WO2019/121147
PCT Pub. Date: Jun. 27, 2019

(65) Prior Publication Data
US 2020/0315990 A1  Oct. 8, 2020

(30) Foreign Application Priority Data
Dec. 22, 2017 (IT) .................. 102017000148931

(51) Int. Cl.
*A61K 31/09* (2006.01)
*A23K 10/32* (2016.01)
*A23K 20/111* (2016.01)
*A23K 20/158* (2016.01)
*A23K 20/195* (2016.01)
*A23K 50/10* (2016.01)
*A23L 29/00* (2016.01)
*A23L 33/00* (2016.01)
*A23L 33/10* (2016.01)
*A23L 33/12* (2016.01)
*A61K 9/00* (2006.01)
*A61P 15/08* (2006.01)
*A61P 31/04* (2006.01)

(52) U.S. Cl.
CPC .............. *A61K 31/09* (2013.01); *A23K 10/32* (2016.05); *A23K 20/111* (2016.05); *A23K 20/158* (2016.05); *A23K 20/195* (2016.05); *A23K 50/10* (2016.05); *A23L 29/03* (2016.08); *A23L 33/12* (2016.08); *A23L 33/127* (2016.08); *A23L 33/40* (2016.08); *A61K 9/0056* (2013.01); *A61P 15/08* (2018.01); *A61P 31/04* (2018.01); *A23V 2002/00* (2013.01)

(58) Field of Classification Search
None
See application file for complete search history.

(56) References Cited

U.S. PATENT DOCUMENTS

2010/0305241 A1  12/2010  Balakshin et al.
2016/0376300 A1  12/2016  Grelier et al.
2017/0152199 A1   6/2017  Feghali et al.

FOREIGN PATENT DOCUMENTS

| JP | 2000191520 A | 7/2000 |
| WO | 2013182751 A1 | 12/2013 |
| WO | 2016005836 A1 | 1/2016 |
| WO | 2016024359 A1 | 2/2016 |
| WO | 2017095316 A1 | 6/2017 |
| WO | 2017210780 A1 | 12/2017 |
| WO | 2018001935 A1 | 1/2018 |

OTHER PUBLICATIONS

Núñez-Flores, et al., Food Hydrocolloids, 30:163. (Year: 2013).*
Lu, et al., Journal of Spectroscopy, Article ID 8951658, pp. 1-15. (Year: 2017).*
Ponomarenko, et al., Holzforschung, 69:795. (Year: 2015).*
Pan, et al., J. Agric. Food Chem., 54:5806. (Year: 2006).*
Raskin et al. (2004) Current Pharmaceutical Design 10, 3419-3429. (Year: 2004).*
Tatiana Dizhbite et al; "Characterization of the radical scavenging activity of lignins natural antioxidants"; Bioresource Technology, Amsterdam, Netherlands, Dec. 1, 2004.
Gosselink, et al; "Analytical Protocols for Characterization of Sulphur-Free Lignin"; Industrial Crops and Products; Netherlands; Dec. 11, 2003.
Kai Wrmeyer, at al; "Comparison of different pretreatment methods for lignocellulosic materials." Bioresource Technology; Netherlands; Nov. 17, 2010.
Pu Yunqiao, et al; "Lignin Structural Alterations in Thermochemical Pretreatments with Limited Delignification" Bienergy Research; United States; Aug. 2, 2015.
Rashid Tazien, et al. "Effect of Temperature on Molecular Weight Distribution of Pyridinium Acetate Treated Kraft Lignin"; Procedia Engineering; Netherlands; Jul. 12, 2016.
Otavio Augusto Titton Dias, et al; "Recent approaches and future trends for lignin-based materials"; Molecular Crystals and Liquid Crystals; United Kingdom; Sep. 22, 2017.
Baurhoo et al., "Effects of Purified Lignin and Mannan Oligosaccharides on Intestinal Integrity and Microbial Populations in the Ceca and Litter of Broiler Chickens," Poultry Science Association Inc., 2007, 9 pages.

* cited by examiner

*Primary Examiner* — Russell G Fiebig
(74) *Attorney, Agent, or Firm* — Dickinson Wright PLLC (57) ABSTRACT

The use of a lignin fraction as a human and animal food supplement ingredient, as well as food supplements comprising the same, are disclosed.

18 Claims, 2 Drawing Sheets

USE OF A LIGNIN FRACTION AS A HUMAN AND ANIMAL FOOD SUPPLEMENT INGREDIENT

FIELD OF THE INVENTION

The present invention concerns the use of a lignin fraction as a human and animal food supplement ingredient, as well as food supplements comprising the same.

STATE OF THE ART

In some industries, for example in the food industry, it is necessary to avoid bacteria proliferation in order to maintain hygienic conditions into the products processed into the industry, for example a food product. In farms, and in slaughterhouses, bacteria proliferations are, on the one hand very common, and on the other hand it is very important to limit and avoid such proliferations.

Known products are often inefficacious against many microorganisms, therefore many different products have to be used, and also known products are often polluting both for the environment and for the product for which they are used.

Product typically used in these cases are antibiotics. However, the overuse and misuse of these medications, as well as a lack of new drug development by the pharmaceutical industry due to reduced economic incentives and challenging regulatory requirements, is considered to be underlying the antibiotic resistance crisis.

Antimicrobial resistance (AMR) is the ability of a microbe to resist the effects of medication previously used to treat them. The term includes the more specific "antibiotic resistance", which applies only to bacteria becoming resistant to antibiotics. Resistant microbes are more difficult to treat, requiring alternative medications or higher doses, both of which may be more expensive or more toxic.

The World Health Organization affirmed that inappropriate use of antibiotics in animal husbandry is an underlying contributor to the emergence and spread of antibiotic-resistant germs, and that the use of antibiotics as growth promoters in animal feeds should be restricted. The World Organisation for Animal Health has added to the Terrestrial Animal Health Code a series of guidelines with recommendations to its members for the creation and harmonization of national antimicrobial resistance surveillance and monitoring programs, monitoring of the quantities of antibiotics used in animal husbandry, and recommendations to ensure the proper and prudent use of antibiotic substances. Another guideline is to implement methodologies that help to establish associated risk factors and assess the risk of antibiotic resistance.

It is therefore felt the need to effectively counteract these bad microorganisms avoiding the use of antibiotics, while at the same time preserving the human and animal health.

SUMMARY OF THE INVENTION

The above object has been achieved by the use of a lignin fraction as an anti-pathogenic agent in human and animal food supplement, as claimed in claim 1.

In this regard, the present invention also concerns a food supplement comprising said lignin fraction and suitable food carriers.

In another aspect, the present invention concerns the food supplement for use in the livestock feeding, wherein said food supplement is administered in an amount effective for improving the quality and shelf life of the meat obtainable from livestock.

In a further aspect, the present invention concerns the food supplement for use in the female livestock feeding, wherein said food supplement is administered in an amount effective for improving the production and quality of milk obtainable from female livestock.

In an additional aspect, the present invention concerns the food supplement for use in the livestock feeding, wherein said food supplement is administered in an amount effective for improving the fertility of livestock.

In a further aspect, the present invention concerns the food supplement for use in the livestock feeding, wherein said food supplement is administered in an amount effective for reducing methane emissions, without impairing digestive efficiency or rumination.

BRIEF DESCRIPTION OF THE FIGURES

The characteristics and the advantages of the present invention will become apparent from the following detailed description, from the working examples provided for illustrative purposes, and from the accompanying figures, wherein.

DETAILED DESCRIPTION OF THE INVENTION

The subject of the invention therefore is the use of a lignin fraction as an anti-pathogenic agent in human and animal food supplement in the prevention and treatment of infections ascribable to food pathogens, wherein said lignin fraction comprises fragments having a weight average molecular weight up to 2,500 Daltons, as measured by Size-Exclusion Chromatography, said fragments comprising up to 13 phenylpropane units on weight average.

Lignin is a class of complex organic polymers that form important structural materials in the support tissues of some algae, vascular plants, included their bark, and herbaceous plants, such as wood (i.e. softwood and hardwood), straw of all cereals, cane bagasse, grass, linen, jute, hemp, or cotton. Lignin can also have mineral source, such as peat, leonardite and coal. Chemically, lignin is a very irregular, randomly cross-linked polymer of phenylpropane units joined by many different linkages, with a weight average molecular weight of 20,000 Daltons or higher. A representative and illustrative lignin fragment (I) containing the most important bonding patterns is shown herein below:

(I)

Said polymer is the result of an enzyme-mediated dehydrogenative polymerization of three phenylpropanoid monomer precursors:

which result in the following moieties, respectively:

Coniferyl alcohol occurs in all species and is the dominant monomer in conifers (softwoods). Deciduous (hardwood) species contain up to 40% synapyl alcohol units while grasses and agricultural crops may also contain coumaryl alcohol units.

Lignin can be categorized to softwood and hardwood lignins according to their raw biomass sources. Raw biomass sources that can be suitable starting materials for obtaining the relevant lignin fraction are any lignin including essentially pure lignin as well as kraft lignin, biomass originating lignin, lignin from alkaline pulping process, lignin from soda process, lignin from organosolv pulping and any combination thereof.

By the expression "essentially pure lignin", it should be understood as at least 90% pure lignin on a dry raw biomass basis, preferably at least 95% pure lignin, the remainder being extractives and carbohydrates such as hemicelluloses as well as inorganic matter.

By the expression "kraft lignin", it is to be understood lignin that originates from kraft black liquor. Black liquor is an alkaline aqueous solution of lignin residues, hemicellulose, and inorganic chemicals used in a kraft pulping process. The black liquor from the pulping process comprises components originating from different softwood and hardwood species in various proportions. Lignin can be separated from the black liquor by different techniques including e.g. precipitation and filtration. Lignin usually begins precipitating at pH values below 11-12. Different pH values can be used in order to precipitate lignin fractions with different properties. These lignin fractions may differ from each other by molecular weight distribution, e.g. $M_w$ and $M_n$, polydispersity, hemicellulose and extractive contents, contents of inorganic material. The precipitated lignin can be purified from inorganic impurities, hemicellulose and wood extractives using acidic washing steps. Further purification can be achieved by filtration.

Alternatively, the lignin is separated from pure biomass. The separation process can begin with liquidizing the biomass with strong alkali followed by a neutralization process. After the alkali treatment, the lignin can be precipitated in a similar manner as presented above.

Alternatively, the separation of lignin from biomass comprises a step of enzyme treatment. The enzyme treatment modifies the lignin to be extracted from biomass. Lignin separated from pure biomass is essentially sulphur-free (sulphur content less than 3%) and thus valuable in further processing.

Preferably, the lignin so separated is also subjected to a depolymerization process in order to further reduce the weight average molecular weight of fragments.

Preferably, the lignin so separated is also subjected to a depolymerization process in order to further reduce the weight and number average molecular weights of fragments. Suitable depolymerization processes include base-catalyzed depolymerization, acid-catalyzed depolymerization, metallic catalyzed depolymerization, ionic liquids-assisted depolymerization, and supercritical fluids-assisted lignin depolymerization.

In preferred embodiments, said lignin fraction is obtained by base-catalyzed depolymerization.

Preferably, said lignin fraction is obtained by subjecting the separated lignin to a base-catalyzed depolymerization at a temperature lower than 300° C. and a pressure lower than 30 MPa.

The pH is set between 11 and 14, by adding a base such as NaOH, KOH, Ca(OH)$_2$, LiOH, K$_2$CO$_3$, or a mixture thereof.

For the purposes of the present invention, the weight average molecular weight ($M_w$) of fragments in the lignin fraction is measured by Size-Exclusion Chromatography (or 'SEC'). SEC employs a stagnant liquid present in the pores of beads as the stationary phase, and a flowing liquid as the mobile phase. The mobile phase can therefore flow between the beads and also in and out of the pores in the beads. The separation mechanism is based on the size of the polymer molecules in solution. Bigger molecules will elute first. Small molecules that can enter many pores in the beads take a long time to pass through the column and therefore exit the column slowly. To determine the molecular weights of the components of a polymer sample, a calibration with standard polymers of known weight must be performed. Values from the unknown sample are then compared with the calibration graph. The retention times depends on the used column material, eluent and how similar the used standards are compared to the samples. In the present invention, the eluent is preferably 0.1 M NaOH.

The lignin fraction of the invention has unexpectedly and surprisingly proved to be very selective and effective against food pathogens, at the same time without negatively affecting the probiotic microorganisms, as shown in the Examples provided below.

Food pathogens are Gram-positive and Gram-negative bacteria and fungi, such as *Escherichia coli, Candida albicans, Pseudomonas aeruginosa, Staphylococcus aureus, Salmonella enterditis, Campylobacter jejuni, Listeria monocytogenes.*

Examples of probiotic microorganisms are *Lactobacillus plantarum, Lactobacillus rhamnosus, Lactobacillus acidophilus, Enterococcus faecium, Saccaromyces boulardii, Bifidobacterium bifidum, Bifidobacterium infantis, Bifidobacterium longum, Bifidobacterium breve, Bifidobacterium lactis, Lactobacillus reuteri, Lactobacillus brevis, Lactobacillus fermentum, Lactobacillus paracasei, Streptococcus thermophilus.*

This means that the lignin fraction of the invention advantageously allows to substitute the antibiotic treatment. Antibiotic-resistance, defined as the emergence (and propagation) of factors of bacterial resistance to antibiotics, is triggered by the selective pressure exerted on microbe populations by an excessive and/or improper use of antibiotics. The lignin fraction as here described has proved to be an effective alternative to the antibiotics for the prevention and treatment of antibiotic-resistant infections.

As it will be seen from the Examples given below, the lignin fraction of the present invention advantageously and surprisingly allows to increase the overall health and wellness of human and animals, especially livestock, while increasing economic performance of the latter, as well as the quality of milk and meat obtainable therefrom. Preferably, said lignin fraction comprises fragments having a weight average molecular weight up to 2,000 Daltons.

In preferred embodiments, said lignin fraction comprises fragments having a weight average molecular weight up to 1,500 Daltons.

In some embodiments, said lignin fraction comprises fragments having a weight average molecular weight down to 150 Daltons.

In preferred embodiments, said lignin fraction comprises fragments having a weight average molecular weight of 150 Daltons to 2,500 Daltons, preferably having a weight average molecular weight of 250 Daltons to 2,000 Daltons, more preferably having a weight average molecular weight of 500 Daltons to 1,800 Daltons.

Preferably in these embodiments, said fragments comprise up to 12 phenylpropane units on weight average, more preferably, up to 11 phenylpropane units on weight average.

The molecular weight of the three phenylpropanoid monomer precursors varies between 150 Da of coumaryl alcohol, 180 Da of coniferyl alcohol, and 210 Da of synapyl alcohol. The average weight is therefore 180 Da and this value has been used as "phenylpropane unit". The $M_w$ values have been divided by 180 Da, thus obtaining the phenylpropane unit numbers on weight average.

Particularly preferred embodiments are those wherein said lignin fraction comprises fragments having a weight average molecular weight of 250 Daltons to 2,000 Daltons and 2 to 11 phenylpropane units on weight average.

In other embodiments, the lignin fraction comprises fragments having a number average molecular weight ($M_n$) up to 2,000 Daltons.

For the purposes of the present invention, the number average molecular weight ($M_n$) of fragments in the lignin fraction is measured by Size-Exclusion Chromatography. Preferably, the lignin fraction comprises fragments having a number average molecular weight ($M_n$) up to 1,500 Daltons.

In preferred embodiments, said lignin fraction comprises fragments having a number average molecular weight of 150 Daltons to 1,000 Daltons.

Without wishing to be bound by any theory, it is believed that lower number average molecular weights mean more active molecules. This is put forward considering that lower molecular weights mean smaller fragments, and smaller fragments mean less crosslinked/shorter fragments, and less crosslinked/shorter fragments mean a higher number of free functional groups thereon, thus more reactive fragments.

Moreover, it is believed that smaller molecules can easily pass through the cell membrane of pathogens and diffuse therewithin, thus significantly increasing the overall effectiveness of the lignin fraction.

Preferably in these embodiments, said fragments comprise up to 11 phenylpropane units on number average, more preferably, up to 8 phenylpropane units on number average.

The molecular weight of the three phenylpropanoid monomer precursors varies between 150 Da of coumaryl alcohol, 180 Da of coniferyl alcohol, and 210 Da of synapyl alcohol. The average weight is therefore 180 Da and this value has been used as "phenylpropane unit". The $M_n$ values have been divided by 180 Da, thus obtaining the phenyl propane unit numbers on number average.

In preferred embodiments, said lignin fraction comprises fragments having a weight average molecular weight ($M_w$) of 150 Daltons to 2,500 Daltons, and fragments having a number average molecular weight ($M_n$) up to 2,000 Daltons.

More preferably, said lignin fraction comprises fragments having a weight average molecular weight ($M_w$) of 150 Daltons to 2,500 Daltons and 2 to 13 phenylpropane units on weight average, and fragments having a number average molecular weight ($M_n$) up to 2,000 Daltons and up to 11 phenylpropane units on number average.

In further embodiments, the lignin fraction has a polydispersity index (PDI) of 1.25 to 6. The polydispersity index (PDI) or heterogeneity index, or simply dispersity, is a measure of the distribution of molecular mass in a given polymer sample. PDI is the weight average molecular weight ($M_w$) divided by the number average molecular weight ($M_n$). It indicates the distribution of individual molecular masses in a batch of polymers. Particularly preferred embodiments are those wherein said lignin fraction comprises fragments having a weight average molecular weight ($M_w$) of 150 Daltons to 2,500 Daltons and 2 to 13 phenylpropane units on weight average, and wherein said lignin fraction has a polydispersity index of 1.25 to 6.

Particularly preferred embodiments are also those wherein said lignin fraction comprises fragments having a number average molecular weight ($M_n$) up to 2,000 Daltons and up to 11 phenylpropane units on number average, and wherein said lignin fraction has a polydispersity index of 1.25 to 6.

The most preferred embodiments are those wherein said lignin fraction comprises fragments having a weight average molecular weight ($M_w$) of 150 Daltons to 2,500 Daltons and 2 to 13 phenylpropane units on weight average, a number average molecular weight ($M_n$) up to 2,000 Daltons and up to 11 phenylpropane units on number average, and wherein said lignin fraction has a polydispersity index of 1.25 to 6.

In particularly preferred embodiments of the present invention, said lignin fraction comprises fragments having a weight average molecular weight ($M_w$) of 800 Daltons to 1,500 Daltons and 4-8 phenylpropane units on weight average, a number average molecular weight ($M_n$) of 300 to 700 Daltons and 2-4 phenylpropane units on number average. In these particularly preferred embodiments, in said lignin fraction, the most abundant phenylpropane units are those from coniferyl alcohol, whereas the less abundant phenylpropane units are those from synapyl alcohol.

The lignin fraction can be in a solid or liquid form.

When the lignin fraction is in a solid form, said solid form can be tablet, mini-tablet, micro-tablet, granule, microgranule, pellet, multiparticulate, micronized particulate, or powder.

When the lignin fraction is in a liquid form, said liquid form is a solvent solution.

Suitable solvents are water, glycols, alcohols, polyalcohols, organic acids, and combinations thereof.

Preferred solvents are water, methanol, ethanol, n-propanol, iso-propanol, n-butanol, isobutanol, allyl alcohol, 1,2-propylene glycol, 1,3-propylene glycol, 1,2-ethylene glycol, polyethylene glycol (PEG), glycerol, lactic acid, polylactic acid, and mixtures thereof.

More preferred solvents are water, 1,2-propylene glycol, 1,3-propylene glycol, 1,2-ethylene glycol, polyethylene glycol (PEG), and mixtures thereof.

In the most preferred embodiments, the solvent is water.

Preferably, when the lignin fraction is in a liquid form, said liquid form has a pH of 8-11, more preferably 9.5-10.5.

In preferred embodiments, the lignin fraction is used in an amount of up to 10 kg per ton of animal feed, more preferably 1-5 kg per ton of animal feed.

In an additional aspect, the present invention also concerns a food supplement comprising the lignin fraction for use as above described, and suitable food carriers.

Said food supplement can be in a solid or liquid form.

When the food supplement is in a solid form, said solid form can be tablet, mini-tablet, micro-tablet, granule, microgranule, pellet, multiparticulate, micronized particulate, or powder.

When the food supplement is in a solid form, said solid form comprises up to 99 wt % of lignin fraction, preferably, 5-90 wt % of lignin fraction.

When the food supplement is in a liquid form, said liquid form can be solution, emulsion, dispersion, suspension, gel, drops, or spray.

When the food supplement is in a liquid form, said liquid form comprises up to 50 wt % of lignin fraction, preferably, 0.1-25 wt % of lignin fraction. This means that the composition is a concentrate that can be suitably diluted in water or directly mixed with animal feed before use, if desired.

Suitable carriers are acidifying agents, acidity correctors, anti-agglomerants, antioxidants, fillers, resistance agents, gelling agents, coating agents, modified starches, sequestering agents, thickeners, sweeteners, thinners, solvents, disaggregating agents, glidants, dyes, binders, lubricants, stabilizers, adsorbents, preservatives, wetting agents, flavors, film-forming substances, emulsifiers, wetting agents, release retardants and mixtures thereof.

In preferred embodiments, the food supplement further comprises a lignin fraction comprising fragments having a weight average molecular weight of 3,500-5,500 Daltons, as measured by Size-Exclusion Chromatography, said fragments comprising up to 40 phenylpropane units on weight average. Preferably, the food supplement further comprises a lignin fraction comprising fragments having a weight average molecular weight of 4,000-5,000 Daltons, as measured by Size-Exclusion Chromatography, said fragments comprising up to 35 phenylpropane units on weight average.

In other preferred embodiments, the food supplement further comprises at least one resin acid. Preferably, said resin acid is abietic acid, dehydroabietic acid, palustric acid, neoabietic acid, pimaric acid, isopimaric acid, sandaropimaric acid, or an ester thereof, or an ether thereof, or an alkali or alkaline-earth salt thereof, or a mixture thereof.

Preferably, the food supplement comprises up to 10 wt % of said at least one resin acid, more preferably up to 7 wt %, on the weight of the food supplement.

Resin acids are present in coniferous trees, and there are three main species of resin acid products, namely Tall Oil Rosin (TOR), Wood Rosin and GUM Rosin. TOR is the resin acid fraction separated by vacuum distillation from Crude Tall Oil (CTO) which is produced by the preparation of pulp. CTO is obtained via acidulation of Crude Tall Oil Soap or Crude Sulphate Soap (TOS). TOS is separated from cooking liquid in pulp mill often called black liqueur during pulping process. Wood Rosin is the fraction separated by steam distillation or other means from dead trees, tree stumps, branches etc. and GUM Rosin is the resin fraction that has been steam distilled or separated by other means from resin harvested often called tapping from a living tree.

Substances containing resin acids and obtained by vacuum distillation from crude tall oil include Distilled Tall Oil (DTO), Tall Oil Fatty Acid (TOFA) and Tall Oil Pitch (TOP). DTO contains 10-40% of resin acids. CTO typically contains 15-70% of resin acids, and the lowest resin acid contents are generally provided by the cooking of mixed wood pulp.

The term "Tall Oil Rosin" or "TOR" should be understood as referring to a composition obtained by distillation of crude tall oil and further refinement of distilled tall oil. TOR typically comprises 60-99% (w/w) resin acids.

The term "Wood Rosin" should be understood as referring to a composition obtained by distillation or other means from dead trees, tree stumps, branches etc. Wood Rosin typically comprises 50-99% (w/w) resin acids.

The term "GUM Rosin" should be understood as referring to a composition obtained by distillation or separated by other means from resin harvested from a living tree. GUM Rosin typically comprises 50-99% (w/w) resin acids.

The term "Distilled Tall Oil" or "DTO" should be understood as referring to a composition obtained by distillation of crude tall oil and further refinement of distilled tall oil. DTO typically comprises 10-60% (w/w) resin acids.

The resin acid based composition TOR, Wood Rosin, GUM Rosin, CTO, TOS and

DTO can also be produced by mixing one or more resin acid compositions and one or more fatty acid compositions in form of oils or fats. Produced resin acid derivatives are for example esters, ethers or alkali metal salts.

Resin acids are known to show many properties, such as antibacterial, anti-inflammatory, antioxidant and anti-bacterial biofilm properties. However, resin acids are poorly stable over time, especially in solid forms, as they are subjected to oxidation, spontaneous ignition and packing.

It has been surprisingly found that when said at least one resin acid is mixed with the lignin fraction of the invention, the resulting mixture, either solid or liquid, is very stable over time and without oxidation, so that it is possible to fully take benefit of the properties of resin acids. This means that in the resulting food supplement comprising the lignin fraction of the invention, not only resin acids are preserved from degradation, but also a synergistic anti-inflammatory effect between lignin fraction and resin acids is observed.

The food supplement can also additionally comprise at least one alkali or alkaline-earth salt of fatty acid $C_{12}$-$C_{24}$, at least one fatty oil, or a mixture thereof. These fatty oil or salt allow a better solubilization of resin acids when liquid form of the food supplement is preferred.

Preferably, said alkali or alkaline-earth salt is a salt of lithium, sodium, potassium, magnesium, calcium, or a mixture thereof.

Preferably, said fatty acid $C_{12}$-$C_{24}$ is lauric acid (C12), tridecylic acid (C13), myristic acid (C14), pentadecylic acid (C15), palmitic acid (C16), margaric acid (C17), stearic acid (C18), oleic acid (C18:1), linoleic acid (C18:2), α-linolenic acid (C18:3), γ-linolenic acid (C18:3), nonadecylic acid (C19), arachidic acid (C20), heneicosanoic acid (C21), behenic acid (C22), tricosylic acid (C23), lignoceric acid (C24), stearidonic acid (C18:4), eicosapentaenoic acid (C20:5), docosahexaenoic acid (C22:6), dihomo-γ-linolenic acid (C20:3), arachidonic acid (C20:4), adrenic acid (C22:4), palmitoleic acid (C16:1), vaccenic acid (C18:1), paullinic acid (C20:1), elaidic acid (Ctrans-18:1), gondoic acid (C20:1), erucic acid (C22:1), nervonic acid (C24:1), mead acid (20:3), or a mixture thereof.

In preferred embodiments, said at least one alkali or alkaline-earth salt of fatty acid $C_{12}$-$C_{24}$ is calcium palmitate, calcium laurate, calcium oleate, calcium soap of palm oil, or a mixture thereof.

Preferably, said at least one fatty oil is hemp oil, canola oil, sunflower oil, olive oil, corn oil, palm oil, coconut oil, pine oil, cottonseed oil, wheat germ oil, soya oil, safflower oil, linseed oil, tung oil, castor oil, soybean oil, peanut oil, rapeseed oil, sesame seed oil, rice germ oil, fish oil, whale oil, marine oil, or a mixture thereof.

Preferably, the food supplement comprises said at least one at least one alkali or alkaline-earth salt of fatty acid $C_{12}$-$C_{24}$, at least one fatty oil, or a mixture thereof in a concentration of 1-100 kg per ton of food supplement.

In another aspect, the present invention concerns the food supplement for use in the livestock feeding, for improving the quality and shelf life of the meat obtainable from livestock. Particularly, the present invention concerns the food supplement for use in the livestock feeding wherein said food supplement is administered in an amount effective for improving the quality and shelf life of the meat obtainable from livestock.

With the term "livestock" in the present invention, it is meant to include both ruminant and non-ruminant animals. Ruminants are herbivorous mammals with a four-chambered stomach, who digest otherwise indigestible plant matter by fermenting it in this complex stomach, and who chew the cud (they cough up balls of semi-digested plant matter and re-chew it to break it down before swallowing it again). They include cattle, sheep, goats, deer, antelope, giraffes and camels and their close relatives such as bison, musk oxen, okapi, and lamas. Non-ruminant animals, including pseudo-ruminant animals, can be swine, horses, chickens, rabbits, turkeys, ducks, geese, quails, pheasants, partridges, as well as fish and shellfish. This means that the food supplement of the invention can be advantageously also used in fish and shellfish feeding, i.e. in aquaculture.

It has been surprisingly observed that livestock fed with the food supplement of the invention gave meat of superior quality, as the natural tendency of the meat to lose redness and yellowness over time was unexpectedly and significantly slackened, at the same time drastically increasing the shelf life and freshness of meat, i.e. even up to 7 days and beyond. Without wishing to be bound by any theory, it is believed that the highly effective antioxidant properties of the lignin fraction of the invention allow to hinder the oxidation process on the meat surface thus counteracting the colour changes and preserving the freshness and edibility of the meat for longer periods of time, in addition to the anti-pathogenic properties above reported.

Colour is an important factor that is commonly used as a quality index to the meat industry and meat science research. Colour has been reported to be one of the most important meat quality attributes and significantly influences purchasing decisions, because consumers use discoloration as an indication of lack of freshness and wholesomeness. Although the quality perceived by consumers does not necessarily coincide with the objective quality, anyway it can cause significant economic losses in the fresh meat market. Colour is also important from the economic point of view, denoting quality to consumers who prefer to purchase meat that is red rather than brown in colour, as the industry loses money due to undesirable colour. As demonstrated in the Examples below, the food supplement of the invention allows to keep very satisfying levels of redness and yellowness of fresh meat for prolonged periods of time.

In a further aspect, the present invention concerns the food supplement for use in the female livestock feeding, for improving the production and quality of milk obtainable from female livestock. Particularly, the present invention concerns the food supplement for use in the female livestock feeding wherein said food supplement is administered in an amount effective for improving the production and quality of milk obtainable from female livestock.

It has been surprisingly observed that female livestock fed with the food supplement of the invention gave milk of superior quality and in a greater amount per day, as shown in the following examples. In fact, the effect of administration of the food supplement in lactating cows is evident, with several events and timelines, based on the following observations about amount and quality of the milk produced:
 increase in the concentration of total polyphenols in milk;
 increase of the daily per animal production of milk;
 reduction, in the acute phase, of the number of somatic cells;
 increase in the absorption capacity of free radicals (TEAC).

The above results are very significant, with a peak in the concentration of total polyphenols of about 250%, an increase of +20.8% in overall milk production, a reduction of −31% in number of somatic cells, and an increase of +33% in TEAC.

It should also be noted that these performances denote a particular sync, concentrating the points of maximum in the neighbourhood of 15-17 days of treatment.

It has been also noted that the supplementation according to the invention has created the conditions for extending its benefits for at least 2 weeks after cessation. The beneficial effect began to wane after about 20 days and is proven by the re-increase in somatic cells in milk.

Typical cow milk contains only traces of polyphenols, therefore it should be very appreciated that unexpectedly the milk obtained from cows fed with the food supplement of the invention contains up to 460 mg/l of polyphenols. Considering that the human requirement of polyphenols is 820 mg/die and the human intake of milk is 250 ml/die on average, the contribution in polyphenols given by the milk of the invention is 114 mg, when typically this is close to zero, as said.

In an additional aspect, the present invention concerns the food supplement for use in the livestock feeding, for improving the fertility of livestock, Particularly, the present invention concerns the food supplement for use in the livestock feeding wherein said food supplement is administered in an amount effective for improving the fertility of livestock.

It has been surprisingly observed that livestock fed with the food supplement of the invention showed a significant increase in the fertility rate for both male and female livestock.

Particularly, for female livestock, such as cows, the fertility results to be increased in terms of conception rate after insemination (at least +15%) and reproductive life length, whereas for male livestock, such as bulls and buffalos, the fertility results to be increased in terms of quality of semen, reproductive paraments and reproductive life length.

In a further aspect, the present invention concerns the food supplement for use in the livestock feeding, for reducing methane emissions, without impairing digestive efficiency or rumination. Particularly, the present invention concerns the food supplement for use in the livestock feeding wherein said food supplement is administered in an amount effective for reducing methane emissions, without impairing digestive efficiency or rumination.

Emissions of the greenhouse gas methane from livestock are larger than previously thought, posing an additional challenge in the fight to curb global warming. Revised calculations of methane produced per head of cattle show that global livestock emissions in 2011 were 11% higher than estimates based on data from the UN's Intergovernmental Panel for Climate Change (IPCC). Besides natural sources such as peatland, wetlands and termites, methane from human activity—approximately two-thirds of the total—is produced in two ways: the odourless and colourless gas leaks during the production and transport of coal, oil and especially natural gas; and, in roughly equal measure, from eructation or belching of ruminants such as cattle and sheep, as well as the decay of organic waste, notably in landfills. Methane accounted for about 16% of global greenhouse gas emissions in 2015, according to the IPCC. Methane is far more potent than $CO_2$ as a greenhouse gas, capturing more of the sun's radiative force, but it persists for less time in the atmosphere. Taking that into account, scientists calculate that over a 100-year period the "global-warming potential" of the gas is 28 times greater than for carbon dioxide. It was noted that methane emissions from livestock have risen most sharply in the rapidly developing regions of Asia, Latin America and Africa. By contrast, the increase has slowed sharply in the US and Canada. It was therefore very appreciated the possibility to reduce the overall production of methane from ruminant livestock and it was at the same time very unexpected the fact that the lignin fraction of the invention allows to achieve this object without impairing digestive efficiency or rumination, as demonstrated in the Examples below.

Preferably, the food supplement is administered in ruminants in a daily dosage comprising up to 100 g of lignin fraction of the invention, more preferably 20-80 g of lignin fraction.

It should be also understood that all the combinations of preferred aspects of the use of lignin fraction of the invention, as well as of the food supplement, and the uses of the same, as above reported, are to be deemed as hereby disclosed.

All combinations of the preferred aspects of the use of lignin fraction of the invention, the food supplement, and the respective uses disclosed above are to be understood as herein described.

Below are working examples of the present invention provided for illustrative purposes.

EXAMPLES $M_w$ and $M_n$ in these Examples have been measured by Size-Exclusion Chromatography according to the following procedure.

Reagents and Materials
    Eluent: 0.1 M NaOH, flow 0.5 ml/min
    Calibration for RI detector: Pullulan standards, $M_p$: 100, 000-1,080 (six standards), where $M_p$ is peak maximum molecular weight
    Calibration for UV-detector (280 nm): PSS standards, polystyrenesulfonate sodium salt, $M_p$ 65,400-891 (six standards). Standards are dissolved into ultra-pure water, concentration should be approximately 5 mg/ml. Injection volume is 20 µl.
    Quality control samples: lignin with known $M_w$ distribution is used.

Equipment and Instruments
    Dionex Ultimate 3000 Autosampler, column compartment, and pump
    Dionex Ultimate 3000 Diode Array Detector
    Reflective Index detector: Shodex RI-101
    Columns: PSS MCX columns: precolumn and two analytical columns: 1000 Å and 100 000 Å, column material is sulfonated divinylbenzen copolymer matrix.
    Syringe filters 0.45 µm and glass sample bottles for STD samples. Sample filtration: Mini-Uniprep syringeless filter device PTFE or Nylon, 0.45 µm. For prefiltration 5 µm syringe filter if needed.
    Measuring bottles Procedure
    Preparation of the eluent
    Ideally, water used to prepare eluents should be high quality deionized water of low resistivity (18 MΩ·cm or better) that contains as little dissolved carbon dioxide as possible. The water must be free of biological contamination (e.g., bacteria and molds) and particulate matter.
    Needle washing with 10% MeOH-water
    Liquid samples
    Strong alkaline liquor samples are diluted 1:100 and filtered with PTFE syringe filters (0.45 µm) to vials. Solid lignin samples are diluted and dissolved into 0.1 M NaOH and filtered with PTFE, 0.45 µm syringe filters. Ready samples are load into autosampler. Injection volume is 20 µl. After samples 1 M NaOH is injected as a sample to clean the column.
    Instrument parameters:
    Flow rate 0.5 ml/min
    Eluent 0.1 M NaOH
    Column oven temperature 30° C.
    Isocratic run
    Run time 48 minutes
    Solid samples
    Solid samples (lignin) are dried overnight in an oven at 60° C., if needed. Approximately 10 mg is weighed into a 10-ml measuring bottle. Sample is dissolved and diluted into 0.1 M NaOH solution and filled into a mark. Sample is filtered with PTFE, 0.45 µm filters. If sample does not dissolve properly, it can be put in a ultrasound water bath or sample can be filtered through a 5 µm syringe filter.

Standard samples for calibration

Approximately 50 mg of each standard is weighed into a 10-ml measuring bottle and ultrapure water is added and filled into a mark. Standards are filtered with PTFE 0.45 µm syringe filters. After running the calibration samples, calibration results are integrated and processed in the processing method and saved. Calibration is linear 1st order calibration.

Quality control samples

For lignin samples, lignin with known $M_w$ distribution is used as a quality control sample. Lignin is dissolved into 0.1 M NaOH and the concentration is approximately 1 mg/ml.

Example 1

Organosolv lignin obtained from Beech wood (*Fagus sylvatica*) was subjected to a base-catalysed depolymerization (BCD). The BCD process is run at 280° C. and 250 bar for 8 minutes at pH 12-14. The resulting lignin product consisted of a liquid fraction and a solid fraction.

These fractions were then separated.

The liquid lignin fraction was an oil and had the following characteristics:

Single Species: *Fagus sylvatica*

| | |
|---|---|
| $M_w$ | 100-300 Da (1-2 phenylpropane units) |
| phenols | 0% |
| guaiacols | 15-20% |
| syringols | 50-60% |
| catechols and metoxycatecols | 5-10% |
| oligomers/unknown | 15-30% |

The solid lignin fraction had the following characteristics:
Single Species: *Fagus sylvatica*

| | |
|---|---|
| $M_w$ | 800-1,500 Da (4-8 phenylpropane units) |
| $M_n$ | 300-700 Da (2-4 phenylpropane units) |

Structures of OH-groups:

| | |
|---|---|
| aliphatic | 0.2-0.4 mmol/g |
| carboxylic | 0.3-0.5 mmol/g |
| condensated and syringyl | 1.0-2.0 mmol/g |
| guaiacyl | 0.4 mmol/g |
| catecholic and p-OH-phenyl | 1.0-1.8 mmol/g |

Example 1a 50 g of the oily lignin fraction (5% w/w) above has been mixed with 950 g of 1,3-propylene glycol, and warmed at 40-50° C.

The mixture has been cooled to room temperature, thus obtaining a viscous solution (shortly referred to as "LMW12").

Example 1b 100 g of the solid lignin fraction (10% w/w) above has been hot-mixed with 800 g of 1,3-propylene glycol, and 100 g of $NH_4OH$ (solution at 30%).

The mixture has been cooled to room temperature and then filtered off, thus obtaining a black solution (shortly referred to as "LMW11").

Example 1c 100 g of the solid lignin fraction (10% w/w) above has been hot-mixed with 835 g of 1,3-propylene glycol, and 65 g of KOH (solution at 20%).

The mixture has been cooled to room temperature and then filtered off, thus obtaining a black solution (shortly referred to as "LMW10").

Example 2

The following lignin fraction has been extracted from Kraft black liquor, said lignin fraction having the following characteristics:
>95% of total solids
Single Species: Southern Pine

| | |
|---|---|
| $M_w$ | 4400-5000 Da (24-28 phenylpropane units) |
| $M_n$ | 1200-1300 Da (6-7 phenylpropane units) |

Structures of OH-groups:

| | |
|---|---|
| aliphatic | 2.1 mmol/g |
| carboxylic | 0.5 mmol/g |
| condensated and syringyl | 1.7 mmol/g |
| guaiacyl | 2.0 mmol/g |
| catecholic and p-OH-phenyl | 4.0 mmol/g |

Example 2a 100 g of the lignin fraction (10% w/w) above has been hot-mixed with 840 g of 1,3-propylene glycol, and 60 g of $NH_4OH$ (solution at 30%).

The mixture has been cooled to room temperature and then filtered off, thus obtaining a black solution (shortly referred to as "OX11").

Example 2b 100 g of the lignin fraction (10% w/w) above has been hot-mixed with 840 g of 1,3-propylene glycol, and 60 g of NaOH (solution at 30%).

The mixture has been cooled to room temperature and then filtered off, thus obtaining a black solution (shortly referred to as "OX10").

Example 3

The antimicrobial activity of the products of Example 1 was evaluated through in vitro test of antimicrobial susceptibility with broth microdilution method (CLSI protocol—Clinical and Laboratory Standards Institute). The Minimum Inhibitory Concentrations (MICs) of 4 products (Blank, LMW 12, LMW 11, LMW 10) were determined in multiwell plates, where Blank is 1,3-propylene glycol only.

The antimicrobial activity of products was tested on the microorganisms (bacteria and fungi) listed below:

| Specific screening biocontrol | |
|---|---|
| Bacteria | Fungi |
| *Escherichia coli* | *Candida albicans* |
| *Pseudomonas aeruginosa* | |
| *Staphylococcus aureus* | |
| *Salmonella enterditis* | |
| *Campylobacter jejuni* | |

Results

The compounds were tested as such and after adjusting the pH to 7 and 8.

All the tests have been carried out in triplicate, giving very similar inhibition results.

The results are summarized into the tables below.

The minimum concentration (μg/ml) of lignin fraction for each product at which the bacterium is inhibited

| | E. coli | S. enterditis | S. aureus | P. aeruginosa | C. jejuni |
|---|---|---|---|---|---|
| Blank | 6.25 | 6.25 | 12.5 | 3.12 | n.a. |
| Blank pH 7 | 18.7 | 18.7 | 6.25 | 18.7 | n.a. |
| Blank pH 8 | 12.5 | 12.5 | 12.5 | 12.5 | 12.5 |
| LMW12 | 0.19 | 2.34 | 0.29 | 0.29 | 25 |
| LMW12 pH 7 | 2.34 | 1.17 | 0.09 | 0.78 | 25 |
| LMW12 pH 8 | 0.78 | 0.78 | 0.09 | 0.19 | 12.5 |
| LMW11 | 0.19 | 0.048 | 0.09 | 0.19 | 0.39 |
| LMW11 pH 7 | 2.34 | 2.34 | 1.56 | 0.09 | 0.39 |
| LMW11 pH 8 | 3.12 | 1.56 | 0.39 | 0.19 | 0.78 |
| LMW10 | 0.59 | 0.19 | 0.15 | 0.19 | 0.19 |
| LMW10 pH 7 | 0.59 | 0.19 | 0.15 | 0.19 | 0.19 |
| LMW10 pH 8 | 0.78 | 1.56 | 0.09 | 0.09 | 0.78 |

The minimum concentration (μg/ml) of lignin fraction for each product at which the fungus is inhibited

| | C. albicans |
|---|---|
| Blank | 12.5 |
| Blank pH 7 | 18.7 |
| Blank pH 8 | 12.5 |
| LMW12 | 1.56 |
| LMW12 pH 7 | 2.34 |
| LMW12 pH 8 | 1.56 |
| LMW11 | 1.56 |
| LMW11 pH 7 | 2.34 |
| LMW11 pH 8 | 1.56 |
| LMW10 | 4.69 |
| LMW10 pH 7 | 4.69 |
| LMW10 pH 8 | 1.56 |

Example 4

Determination of the Minimum Inibitory Concentration

The Minimum Inibitory Concentration (MIC) of the lignin fraction of Example 1b was evaluated against 5 probiotic microorganisms through in vitro test of antimicrobial susceptibility with broth microdilution method (CLSI protocol—Clinical and Laboratory Standards Institute).

The microorganisms used were *Lactobacillus plantarum, Lactobacillus rhamnosus, Lactobacillus acidophilus, Enterococcus faecium,* and *Saccaromyces boulardii.*

A positive control of antimicrobial activity using Ceftriaxone (for bacteria) or Fluconazole (for yeast) was prepared for all tests. The results are summarized into the tables below. The samples were diluted and the growth (+) and the inhibition of the growth (−) were evaluated in the different dilutions. The grey square represents the minimum concentration where the inhibition of the growth is observed (MIC).

*Lactobacillus plantarum*:

| MIC % (v/v) | | | | | | | | | | | | | | | |
|---|---|---|---|---|---|---|---|---|---|---|---|---|---|---|---|
| 25 | 12.5 | 6.25 | 3.12 | 1.56 | 0.78 | 0.39 | 0.19 | 0.098 | 0.048 | 0.024 | 0.012 | 0.006 | 0.003 | 0.0015 | 0.00075 |
| − | − | − | − | − | − | + | + | + | + | + | + | + | + | + | + | where 0.78 v/v corresponds to 780 μg/ml

*Lactobacillus rhamnosus*:

| MIC % (v/v) | | | | | | | | | | | | | | | |
|---|---|---|---|---|---|---|---|---|---|---|---|---|---|---|---|
| 25 | 12.5 | 6.25 | 3.12 | 1.56 | 0.78 | 0.39 | 0.19 | 0.098 | 0.048 | 0.024 | 0.012 | 0.006 | 0.003 | 0.0015 | 0.00075 |
| − | − | − | − | − | − | + | + | + | + | + | + | + | + | + | + | where 0.78 v/v corresponds to 780 μg/ml

*Lactobacillus acidophilus*:

| MIC % (v/v) | | | | | | | | | | | | | | | |
|---|---|---|---|---|---|---|---|---|---|---|---|---|---|---|---|
| 25 | 12.5 | 6.25 | 3.12 | 1.56 | 0.78 | 0.39 | 0.19 | 0.098 | 0.048 | 0.024 | 0.012 | 0.006 | 0.003 | 0.0015 | 0.00075 |
| − | − | − | − | − | − | − | + | + | + | + | + | + | + | + | + | where 0.78 v/v corresponds to 780 μg/ml

*Enterococcus faecium*:

| MIC % (v/v) | | | | | | | | | | | | | | | |
|---|---|---|---|---|---|---|---|---|---|---|---|---|---|---|---|
| 25 | 12.5 | 6.25 | 3.12 | 1.56 | 0.78 | 0.39 | 0.19 | 0.098 | 0.048 | 0.024 | 0.012 | 0.006 | 0.003 | 0.0015 | 0.00075 |
| − | − | − | + | + | + | + | + | + | + | + | + | + | + | + | + | where 6.25 v/v corresponds to 6,250 µg/ml
*Saccaromyces boulardii*:

| MIC % (v/v) | | | | | | | | | | | | | | | |
|---|---|---|---|---|---|---|---|---|---|---|---|---|---|---|---|
| 25 | 12.5 | 6.25 | 3.12 | 1.56 | 0.78 | 0.39 | 0.19 | 0.098 | 0.048 | 0.024 | 0.012 | 0.006 | 0.003 | 0.0015 | 0.00075 |
| − | + | + | + | + | + | + | + | + | + | + | + | + | + | + | + | where 25 v/v corresponds to 25,000 µg/ml

As it can be seen above, it is clear that the lignin fraction of the invention does not negatively affect probiotic microorganisms.

Example 5

Determination of Prebiotic Activity

The lignin fraction of Example 1b also presented prebiotic activity on *E. faecium*.

The prebiotic activity of lignin fraction of Example 1b was tested at concentrations below the related MIC obtained versus the probiotic bacteria *E. faecium*.

Concentrations lignin fraction used for the prebiotic test:

| lignin fraction of Example 1b (g/L) - *E. faecium* | | | | | |
|---|---|---|---|---|---|
| 3.7 | 2.5 | 1.9 | 1.25 | 0.9 | 0.62 |

Prebiotic activity was evaluated through a quantitative equation (prebiotic index) in which the growth of probiotic and enteric bacteria (*E. coli, S. thyphimurium*) were compared in the presence of lignin fraction of Example 1b.

The prebiotic index was calculated as reported below:

$$\text{Prebiotic index} = \left\lVert \frac{\left[\text{probiotic log10}\frac{cfu}{ml} \text{ on the prebiotic at 24 hr} - \text{probiotic log10}\frac{cfu}{ml} \text{ on the prebiotic at 0 hr}\right]}{\text{probiotic log10}\frac{cfu}{ml} \text{ on glucose at 24 hr} - \text{probiotic log10}\frac{cfu}{ml} \text{ on glucose at 0 hr}} \right. -$$

$$\left. \frac{\left[\text{enteric log10}\frac{cfu}{ml} \text{ on the prebiotic at 24 hr} - \text{enteric log10}\frac{cfu}{ml} \text{ on the prebiotic at 0 hr}\right]}{\text{enteric log10}\frac{cfu}{ml} \text{ on glucose at 24 hr} - \text{enteric log10}\frac{cfu}{ml} \text{ on glucose at 0 hr}} \right\rVert$$

wherein the first term denotes the growth of probiotic, whereas the second term denotes the growth of enteric bacterium.

The prebiotic compound is able to selectively enhance the growth of specific probiotic bacteria conversely for enteric bacteria that does not use the compound to improve the growth, hence Prebiotic index >0 indicates a prebiotic activity.

Results on prebiotic activity (*S. thyphimurium* was used as enteric bacterium):

| | *E. faecium* | | |
|---|---|---|---|
| lignin fraction of Example 1b (g/L) | 1.9 | 1.25 | 0.9 |
| Prebiotic index | 2.2 | 0.4 | 0.3 |

Example 6

Use of Lignin Fraction in Beef Feeding

Experimental Design, Animal Management, Meat Sampling and Analysis

The trial was conducted on 40 male beef, randomly subdivided in 2 groups, one as control group and one as experimental group. Both groups had the same feeding ratio, composed of commercial feed (calculated on the basis of the 2% of live weight) and ad libitum mixed hay. Before starting, all animals were weighted, and, accordingly their live weight, were subdivided in the two groups in order to obtain the same mean live weight at the start of the trial. The trial last 120 days, the 120 days before animal slaughtering. The experimental group, differently from the control group, assumed daily the lignin fraction of Example 1b for a quantity of 35 g per animal in the first 90 days and 70 g per animal in the other 30 days.

All animals were weighted monthly in order to evaluate the final live weight, the monthly weight gain and the food conversion index. Moreover, during the trial, also blood samples were collected in order to evaluate the blood cell count and biochemical profile.

Animals were transported and slaughtered at a European Community-approved abattoir in compliance with European Community laws on Animal Welfare in transport (1/2005EC) and the European Community regulation on Animal Welfare for slaughter of commercial animals (1099/2009EC). Immediately after slaughter, carcasses were stored at 4° C. for 24 h. Afterwards, samples of Longissimus thoracis et lumborum (LTL) muscle between the 13th and 18th thoracic vertebra (about 4 kg of each sample) were taken for analysis.

Meat of each animal was conserved at 4° C. and, during its maturation, at days 3, 6, 9 and 14, colorimetric parameters were measured. The surface meat colour was determined according to the CIE L*, a*, b* (CIE, 1976) colour system using a Minolta CR-300 colorimeter (light source D65; Minolta Camera Co. Ltd., Osaka, Japan). Reflectance measurements were collected from a 0° viewing angle with A-pulsed xenon arc lamp with a reading surface of 8 mm diameter. For each sample of meat, three measurements were performed at three different points. Three measurements were obtained at each point, performed by rotating the detector system by 90° compared to the previous one, giving a total of nine measurements per sample. The colorimeter was calibrated on the Hunter-lab colour space system using a white title (L*=99.2, a*=1.0, b*=1.9). The a* and b* values were used to determine chroma=(a2+b2)1/2 and hue(°)=tan−1(b/a) according to De Palo et al. ("Colour changes in meat of foals as affected by slaughtering age and post-thawing time", 2012, Asian-Australasian Journal of Animal Sciences, 25, 1775-1779).

Moreover, rheologic parameters were measured. The pH was recorded using a portable pH meter with glass electrode shaped to easily penetrate meat (Carlo Erba pH 710;

Carlo Erba Reagenti, Milano, Italy). Before each measurement, the pH meter was automatically calibrated for muscle temperature and using solutions with 4 and 7 pH values (Crison, Lainate, Italy). The water holding capacity (WHC), cooking losses and Warner-Bratzler shear force (WBSF) were measured as described by De Palo et al. ("Effect of nutritive level on carcass traits and meat quality of IHDH foals", 2014 Animal Science Journal, 85, 780-786).

Moreover, the in vitro digestion was done in order to evaluate the total gas production over 24 hours.

Results

Here are reported the more interesting results about meat quality, in particular colorimetric profile, and in vitro digestion gas production.

Figure 1:
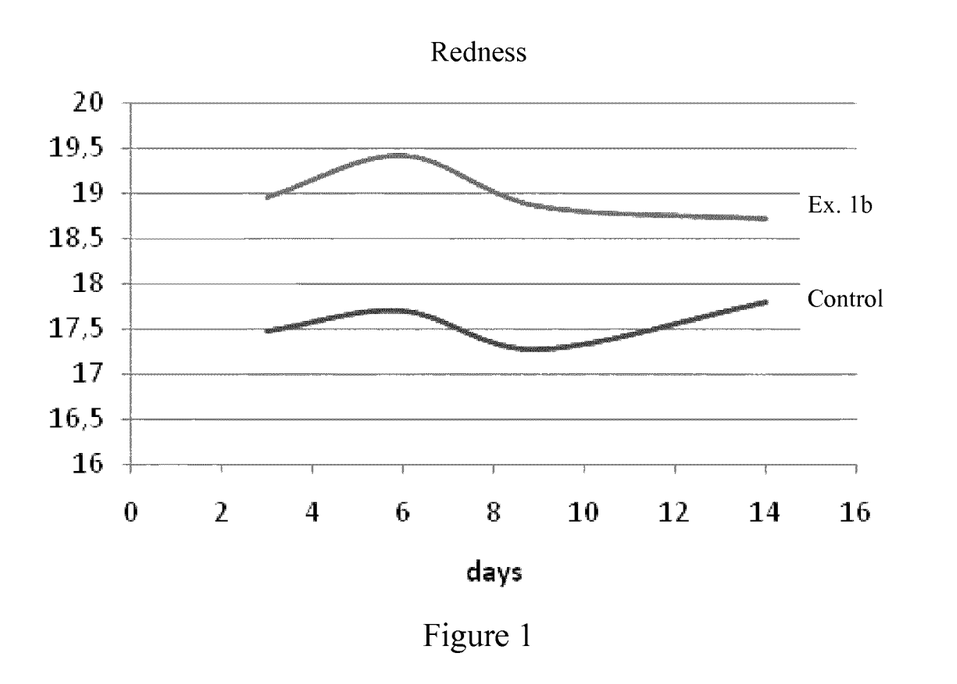
FIG. 1 shows the redness profile in meat of control and experimental groups during 14 days of ageing, as per Example 6.

In particular, as reported in FIG. 1, redness showed to be different between the two groups. Meat obtained by beefs fed with added lignin fraction, showed higher redness during all the maturation time, until the 14th day. Recent work has attributed the effects of diet on muscle colour to either altered glycogen storage, refrigeration rate, or antioxidant accumulation, all of which can ultimately relate to muscle's fundamental intrinsic colour traits. Usually, during ageing, redness tends to decrease, showing a falling trend. This is not the case in the meat samples from the experimental group. The decrease of redness on meat surface is due to the biochemical phenomena which occurred with the exposition of myoglobin pigment to air. The myoglobin oxidation causes darkening processes on meat. In the case of experimental group, the antioxidant assumption by feed in animals gives a higher meat redness that is also positively evaluated by consumers.

Figure 2:
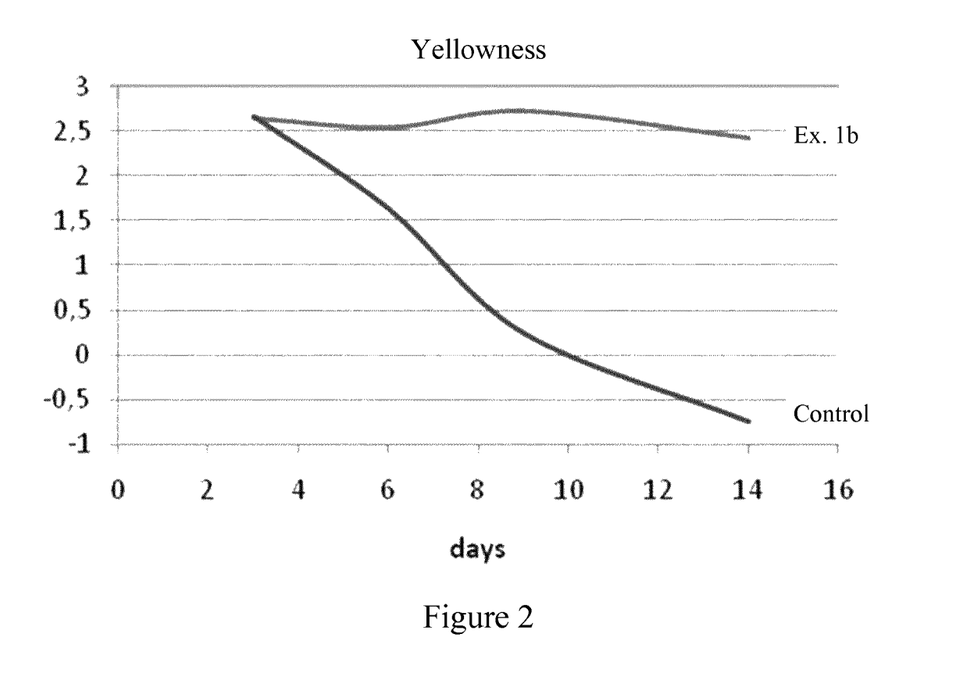
FIG. 2 shows the yellowness profile in meat of control and experimental groups during 14 days of ageing, as per Example 6.

FIG. 2 reported the yellowness trend. Animals of control group showed a falling trend of this index, differently animals that assumed the antioxidant showed a stability of yellowness, with no changes in its values during ageing. Yellowness is closely linked to intramuscular fat quantity and quality. Considering the same feed assumed and the similar weight gain and live weight at slaughter, and considering the similar chemical composition of meat, no differences in intramuscular fat content were observed between the two groups. Differently, these differences can be due to a different intramuscular fat quality, with different fatty acid profiles. In fact, differences in yellowness stability can be probably due to the development of lipid oxidation processes following the release of lipolytic enzymes in the intercellular interstices and with oxide-reducing activities within the fibres.

Figure 3:
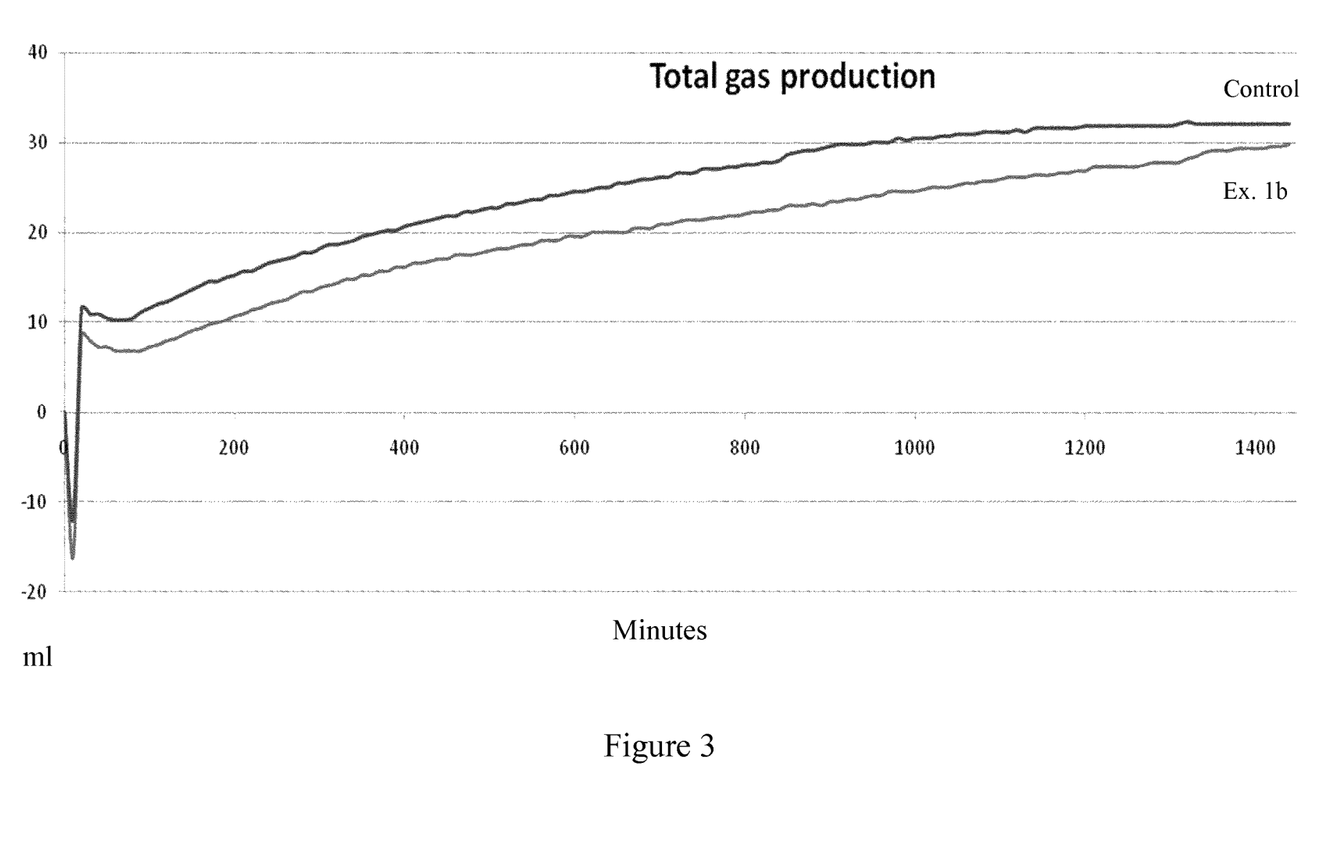
FIG. 3 shows the total gas production during 24 hours of in vitro digestion of rumen fluid, as per Example 6.

FIG. 3 reported the total gas production (ml) in 24 hours of in vitro digestion of rumen fluid. Animals of experimental group showed, in all times, a lower gas production, with a production of 2864 ml compared to 3545 ml of the control group, therefore with a surprising gas reduction of about 20%. Different studies showed how, some antioxidant used in cow feeding had the activity to reduce the microbial replication reducing also the digestion activity. This aspect results in lower productions of both milk and meat, due to the lower digestion activity in the rumen. In the case of experimental group, the lower gas production unexpectedly did not result into a lower meat production considering that live weight at slaughter, monthly weight gain and dressing percentage did not change between groups. For this reason, it is believed that the lower gas produced could be the methane gas, considering that a reduction in volatile fatty acids should give a lower conversion in meat and so in live weight.

Example 7

Evaluation of Livestock Fertility and Evaluation of the Quality of Milk Obtainable from Cows Fed with the Lignin Fraction of the Invention The aim of this test was to use the lignin fraction of Example 1b for increasing the health of the herd of cows, increasing economic performance and the quality of milk.

Test duration: 28 days, dosing with 30 grams a day per cow

Description of the Test Sample:

The Friesian herd was composed by an average of 85 cows in milking, 20 dry cows and related corporate comeback.

The dairy cows were under stabulation conditions in a comfortable structure, made up with straw bunks in both the inner part and in the outer covered by a canopy structure.

Dry cows bred in a permanent facility adjacent to straw bedding in the rest and delivery area, a central paddock for walking and covered shelter for the feed zone.

All areas offer plenty of space for movement for rest and access to the manger.

Company attentive to genetics leading to sound choices geared to the longevity of the garments and the improvement of milk quality.

Unifeed a single group:
Corn silage,
Lucerne hay (purchased)
Corn flour,
On permanent pasture hay,
Soy, core,
Supplement and tampons.

In 2014 production: 114 tons of milk per cow (AIA data source).

The Health Status of the Herd at the Beginning of the Test:

The herd comes from a summer quite critical, characterized by a very long warm period, about 50-60 days without rain, with very high temperatures and especially high humidity. Although they are implemented all possible environmental conditioning systems, cows accused various swallowed declines resulting in:
decrease in the total production of milk,
decrease of the casein and fat in the milk,
greater presence of lameness;

progressive increase in cell count, which reached a peak 577,000 cells.

Cow Fertility: negative impact with difficulty in the highlighting of heats and low conception rates.

Remarks:

Try: integrated the entire beef herd in lactation with average attendance of 77 heads. average length of the whole lactation period days fluctuated from 180 to 185.

At the start of the test, the health status of the herd was not optimal:

Some cattle had just passed the flu, characterized by diarrhea and decreased appetite;

Are 7 cows with lameness of medium severity.

No problem for the gradual introduction of the lignin fraction in the mixed unifeed, ingestion rose gradually to stabilize after the 1st week.

Consequences: fast recovery of those animals that had accused the malaise due to the flu and was lameness, as certified by the podiatrist doctor.

Increased ingestion, immediately the milk production increased and the physical tone of the animals.

Somatic cell count (SCC), constantly monitored in the company, either by the farmer that the dairy farm through levies on the quality data, the initial 240/250 thousand cells has dropped to 120 thousand, in the 2nd week, and reached steady around 140/150 thousand cells until the end of the test.

Fast: readjustment of the fat and casein in milk returned to more appropriate values for the company.

Increase in general health status of the herd.

Increase in overall fertility.

Milk Production Performance:

Milk production starts on day 0 from a value of 27.83 l/head, reaching day 35 the maximum value of 33.41 l/head.

Increase in daily production per capita recorded at day 35 from start of administration of lignin fraction was +20.08% compared with the initial per capita production.

Overall, the rate of increase in production was of +138 g/head per day.

Maximum daily increase in absolute terms was recorded from the day 16-17 (+2.43 l/head).

Milk Quality Performance:

increase in the concentration of total polyphenols in milk;
increase of the daily per animal production of milk;
reduction, in the acute phase, of the number of somatic cells;
increase in the absorption capacity of free radicals (TEAC).

The above results are very significant, with a peak in the concentration of total polyphenols of about 250%, an increase of +20.8% in overall milk production, a reduction of −31% in number of somatic cells, and an increase of +33% in TEAC.

It should also be noted that these performances denote a particular sync, concentrating the points of maximum in the neighbourhood of 15-17 days of treatment.

It has been also noted that the supplementation according to the invention has created the conditions for extending its benefits for at least 2 weeks after cessation. The beneficial effect began to wane after about 20 days and is proven by the re-increase in somatic cells in milk.

Typical cow milk contains only traces of polyphenols, therefore it should be very appreciated that unexpectedly the milk obtained from cows fed with the food supplement of the invention contains up to 457 mg/l of polyphenols.

Considering that the human requirement of polyphenols is 820 mg/die and the human intake of milk is 250 ml/die on average, the contribution in polyphenols given by the milk of the invention is 114 mg, when typically this is close to zero, as said.

The invention claimed is:

1. A human or animal food supplement comprising a lignin fraction as an anti-pathogenic agent against infections ascribable to food pathogens, wherein said lignin fraction includes a single species, the single species is *Fagus* sylvatic and contains synapyl alcohol units, said lignin fraction is depolymerized, said lignin fraction comprises fragments having a weight average molecular weight up to 2,500 Daltons, as measured by Size-Exclusion Chromatography, and said fragments comprising up to 13 phenylpropane units on weight average.

2. The food supplement of claim 1, wherein the lignin fraction is an anti-pathogenic agent against food pathogens comprising *Escherichia coli, Candida albicans, Pseudomonas aeruginosa, Staphylococcus aureus, Salmonella enterditis, Campylobacter jejuni, Listeria monocytogenes*, without negatively affecting probiotic microorganisms.

3. The food supplement of claim 1, wherein the lignin fraction comprises fragments having a weight average molecular weight of 150 Daltons to 2,500 Daltons, said fragments comprising up to 12 phenylpropane units on weight average.

4. The food supplement of claim 1, wherein the lignin fraction comprises fragments having a number average molecular weight up to 2,000 Daltons, as measured by Size-Exclusion Chromatography, said fragments comprising up to 11 phenylpropane units on number average.

5. The food supplement of claim 4, wherein said lignin fraction comprises fragments having a number average molecular weight of 150 Daltons to 1,000 Daltons.

6. The food supplement of claim 1, wherein the lignin fraction is supplemented in an amount of up to 10 kg per ton of animal feed.

7. The food supplement of claim 1, further comprising suitable food carriers.

8. The food supplement of claim 1, further comprising a lignin fraction comprising fragments having a weight average molecular weight of 3,500-5,500 Daltons, as measured by Size-Exclusion Chromatography, said fragments comprising up to 40 phenylpropane units on weight average.

9. The food supplement of claim 1, further comprising at least one resin acid, said resin acid being abietic acid, dehydroabietic acid, palustric acid, neoabietic acid, pimaric acid, isopimaric acid, sandaropimaric acid, or an ester thereof, or an ether thereof, or an alkali or alkaline-earth salt thereof, or a mixture thereof.

10. The food supplement of claim 1, further comprising at least one alkali or alkaline-earth salt of fatty acid $C_{12}$-$C_{24}$, at least one fatty oil, or a mixture thereof.

11. The food supplement of claim 1, said food supplement being for supplementing livestock feeding, wherein said food supplement is to be supplemented in an amount effective for improving the quality and shelf life of the meat obtainable from livestock.

12. The food supplement of claim 1, said food supplement being for supplementing female livestock feeding, wherein said food supplement is to be supplemented in an amount effective for improving the production and quality of milk obtainable from female livestock.

13. The food supplement of claim 1, said food supplement being for supplementing livestock feeding, wherein said food supplement is to be supplemented in an amount effective for improving the fertility of livestock.

14. The food supplement of claim 1, said food supplement being for supplementing livestock feeding, wherein said food supplement is to be supplemented in an amount effective for reducing methane emissions, without impairing digestive efficiency or rumination.

15. The food supplement of claim 1, wherein said food supplement is to be supplemented in ruminants in a daily dosage comprising up to 100 g of lignin fraction.

16. The food supplement of claim 15, wherein said food supplement is to be supplemented in ruminants in a daily dosage comprising 20-80 g of lignin fraction.

17. The human or animal food supplement of claim 1, wherein said lignin fraction is an oil, said lignin fraction comprises fragments having a weight average molecular weight ranging from 100 to 300 Daltons, as measured by Size-Exclusion Chromatography, and said fragments comprise up to 2 phenylpropane units on weight average.

18. The human or animal food supplement of claim 1, wherein said lignin fraction is a solid, said lignin fraction comprises fragments having a weight average molecular weight ranging from 800 to 1,500 Daltons, as measured by Size-Exclusion Chromatography, and said fragments comprise 4 to 8 phenylpropane units on weight average.

* * * * *